United States Patent [19]

Riese et al.

[11] Patent Number: 5,669,444
[45] Date of Patent: Sep. 23, 1997

[54] CHEMICALLY INDUCED STIMULATION OF COAL CLEAT FORMATION

[75] Inventors: Walter C. Riese, Katy; Stephen V. Bross, Sugar Land, both of Tex.

[73] Assignee: Vastar Resources, Inc., Houston, Tex.

[21] Appl. No.: 594,725

[22] Filed: Jan. 31, 1996

[51] Int. Cl.$^6$ ............ E21B 43/17; E21B 43/26; E21B 43/27; E21B 43/40
[52] U.S. Cl. ............ 166/263; 166/245; 166/268; 166/271; 166/305.1; 166/308
[58] Field of Search ............ 166/245, 263, 166/268, 271, 305.1, 308; 299/4, 5

[56] References Cited

U.S. PATENT DOCUMENTS

| | | | |
|---|---|---|---|
| 4,032,193 | 6/1977 | Drinkard et al. | 299/4 |
| 4,043,395 | 8/1977 | Every et al. | 166/268 X |
| 4,245,699 | 1/1981 | Steeman | 166/271 |
| 4,424,863 | 1/1984 | White | 166/268 |
| 4,537,252 | 8/1985 | Puri et al. | 166/272 |
| 4,662,439 | 5/1987 | Puri et al. | 166/272 |
| 4,662,443 | 5/1987 | Puri et al. | 166/261 |
| 4,747,642 | 5/1988 | Gash et al. | 166/256 |
| 4,762,543 | 8/1988 | Pantermucehl et al. | 62/28 |
| 4,765,407 | 8/1988 | Yuvancic | 166/268 |
| 4,883,122 | 11/1989 | Puri et al. | 166/263 |
| 5,014,788 | 5/1991 | Puri et al. | 166/280 |
| 5,099,921 | 3/1992 | Puri et al. | 166/271 X |
| 5,332,036 | 7/1994 | Shirley et al. | 166/268 |
| 5,417,286 | 5/1995 | Puri et al. | 166/308 |
| 5,419,396 | 5/1995 | Palmer et al. | 166/250 |
| 5,439,054 | 8/1995 | Chaback et al. | 166/252 |
| 5,454,666 | 10/1995 | Chaback et al. | 405/52 |
| 5,494,108 | 2/1996 | Palmer et al. | 166/308 |
| 5,501,273 | 3/1996 | Puri | 166/252 |
| 5,513,707 | 5/1996 | Shaw et al. | 166/305.1 X |

OTHER PUBLICATIONS

SPE 20732 paper entitled "Enhanced Coalbed Methane Recovery", R. Puri and D. Yee, presented at the 65th Annual Technical conference and Exhibition of the society of Petroleum Engineers, New Orleans, LA, Sep. 23–26, 1990.

*Primary Examiner*—George A. Suchfield
*Attorney, Agent, or Firm*—F. Lindsey Scott

[57] ABSTRACT

A method for increasing the production of methane from a subterranean coal formation by chemically stimulating the formation of cleats in the coal formation in order to facilitate removal of formation water, and increase the rate of methane production from the coal formation is disclosed. The method comprises injecting an aqueous oxidant solution into the coal formations to stimulate the formation of cleats in the coal formation; and thereafter producing methane from the coal formations at an increased rate. The aqueous oxidant solution comprises hypochlorite, metallic salts of hypochlorous acid, hydrogen peroxide, ozone, oxygen and combinations thereof.

19 Claims, 3 Drawing Sheets

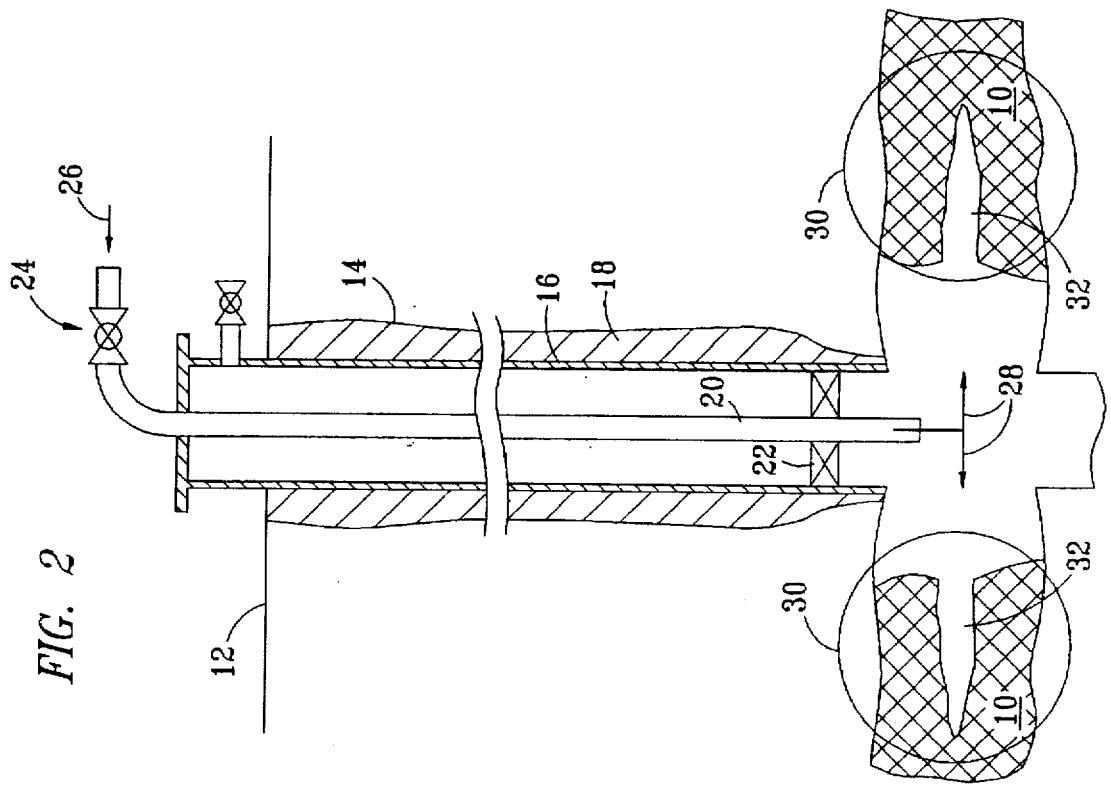
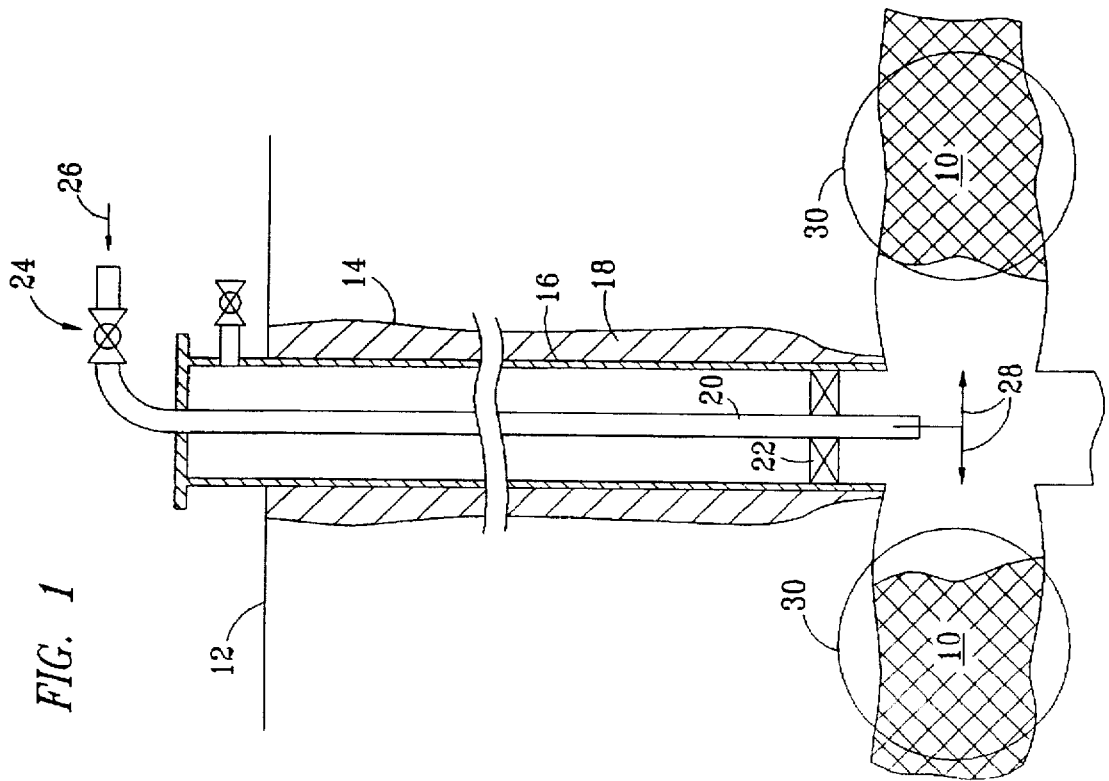

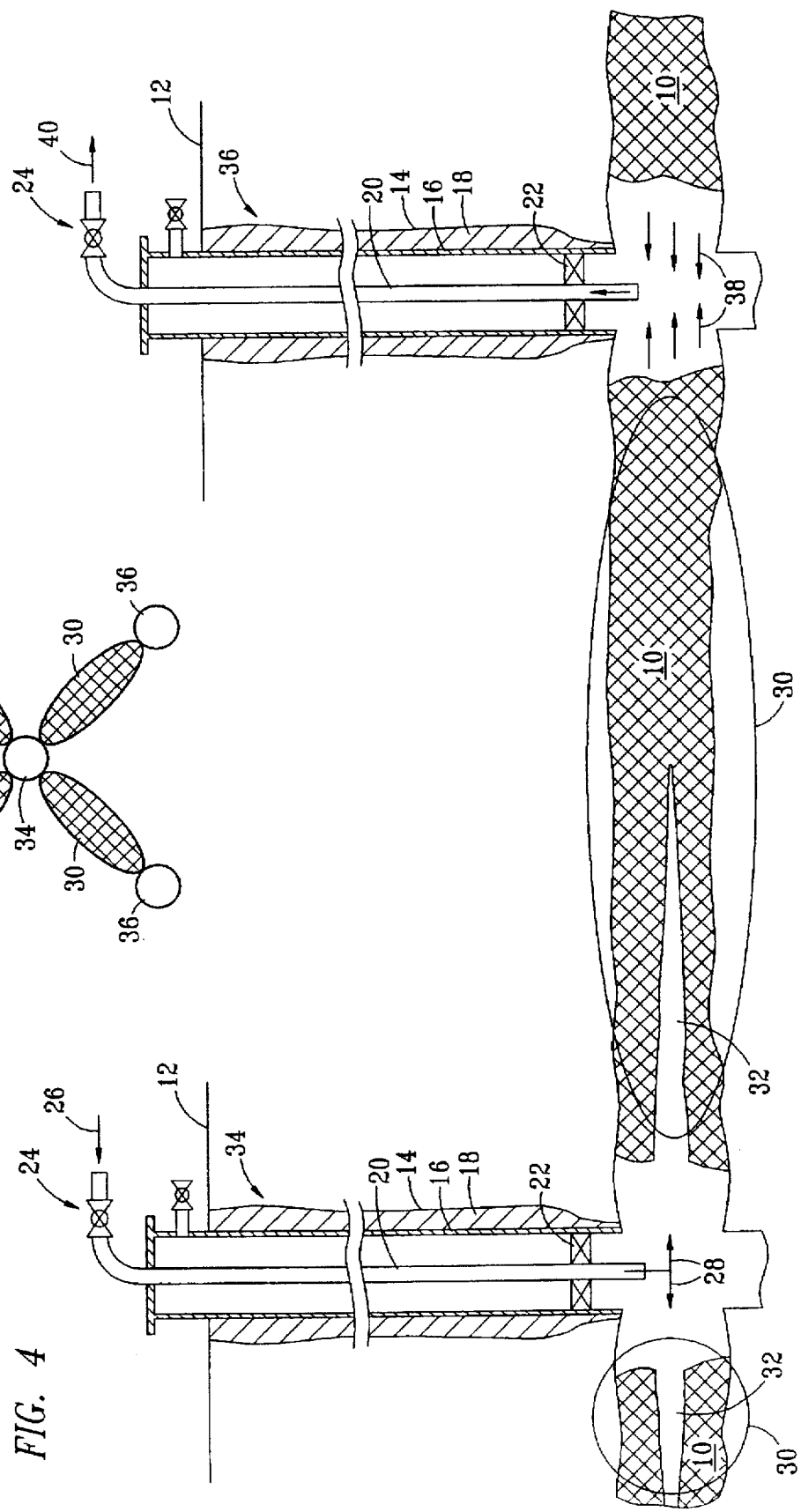

CHEMICALLY INDUCED STIMULATION OF COAL CLEAT FORMATION

BACKGROUND OF THE INVENTION

1. Field of the Invention

This invention relates to methods for increasing the rate of production of methane from subterranean coal formations by chemically stimulating the cleat system in the coal formation to increase the production rate of methane from the coal formation.

2. Brief Description of the Prior Art

Substantial quantities of methane gas are found in subterranean coal formations.

A variety of processes have been used in attempts to recover the methane from the coal formations more efficiently.

The simplest process is the pressure reduction process wherein a borehole is drilled into a coal formation from the surface and methane is withdrawn from the borehole by reducing the pressure to cause methane to be desorbed from and flow from the coal formation into the borehole and to the surface. This method is not efficient because coal formations are generally not extremely porous and the methane is generally not found in the pores of the coal formation but is absorbed onto the coal. While methane can be produced from coal formations by this process, the production of methane is relatively slow.

In some coal formations, the natural permeability is sufficient to allow the removal of in situ water to permit the enhanced recovery of methane. In such formations, cleat systems developed during the coal bed diagenesis provide channel ways through which water and methane migrate to the production wells for removal. This removal of water or "de-watering" of the coal formations removes water from the channel ways and permits the flow of methane through the channel ways and to a production well at a greater rate.

Many coal formations do not have extensively developed cleat systems or have cleat systems which are not fully developed. These coal formations have very low permeability to water and do not yield their water at significant rates. As a result, the water fills the channels, and the recovery of methane from such coal formations is difficult or impossible at significant rates.

Accordingly, continuing efforts have been directed to the development of methods for recovering methane from such coal formations at an increased rate.

SUMMARY OF THE INVENTION

According to the present invention, the rate of recovery of methane from such water-containing subterranean coal formations is increased by positioning at least one well from the surface into the coal formation; injecting an aqueous oxidant solution into the coal formation; maintaining the aqueous oxidant solution in the coal formation for a selected time to stimulate the formation or enhancement of a cleat system in the coal formation; and, producing methane from the coal formation at an increased rate.

The aqueous oxidant solution comprises hypochlorite, metallic salts of hypochlorous acid, hydrogen peroxide, ozone, oxygen and combinations thereof.

The rate of production of methane from water-containing subterranean coal formations penetrated by at least one injection well and at least one production well is increased by:

a) Injecting an aqueous oxidant solution into the coal formation through the injection well; and d) Producing methane from the coal formation through the production well at an increased rate.

BRIEF DESCRIPTION OF THE DRAWINGS

FIG. 1 is a schematic diagram of a well penetrating a subterranean coal formation from the surface.

FIG. 2 is a schematic diagram of a well penetrating a subterranean coal formation from the surface wherein the coal formation has been fractured.

FIG. 4 is a schematic diagram of an injection well and a production well penetrating a subterranean coal formation from the surface wherein the coal formation has been fractured from the injection well.

FIG. 5 is a schematic layout of a 5-spot injection and production well pattern.

DESCRIPTION OF PREFERRED EMBODIMENTS

Figure 3:
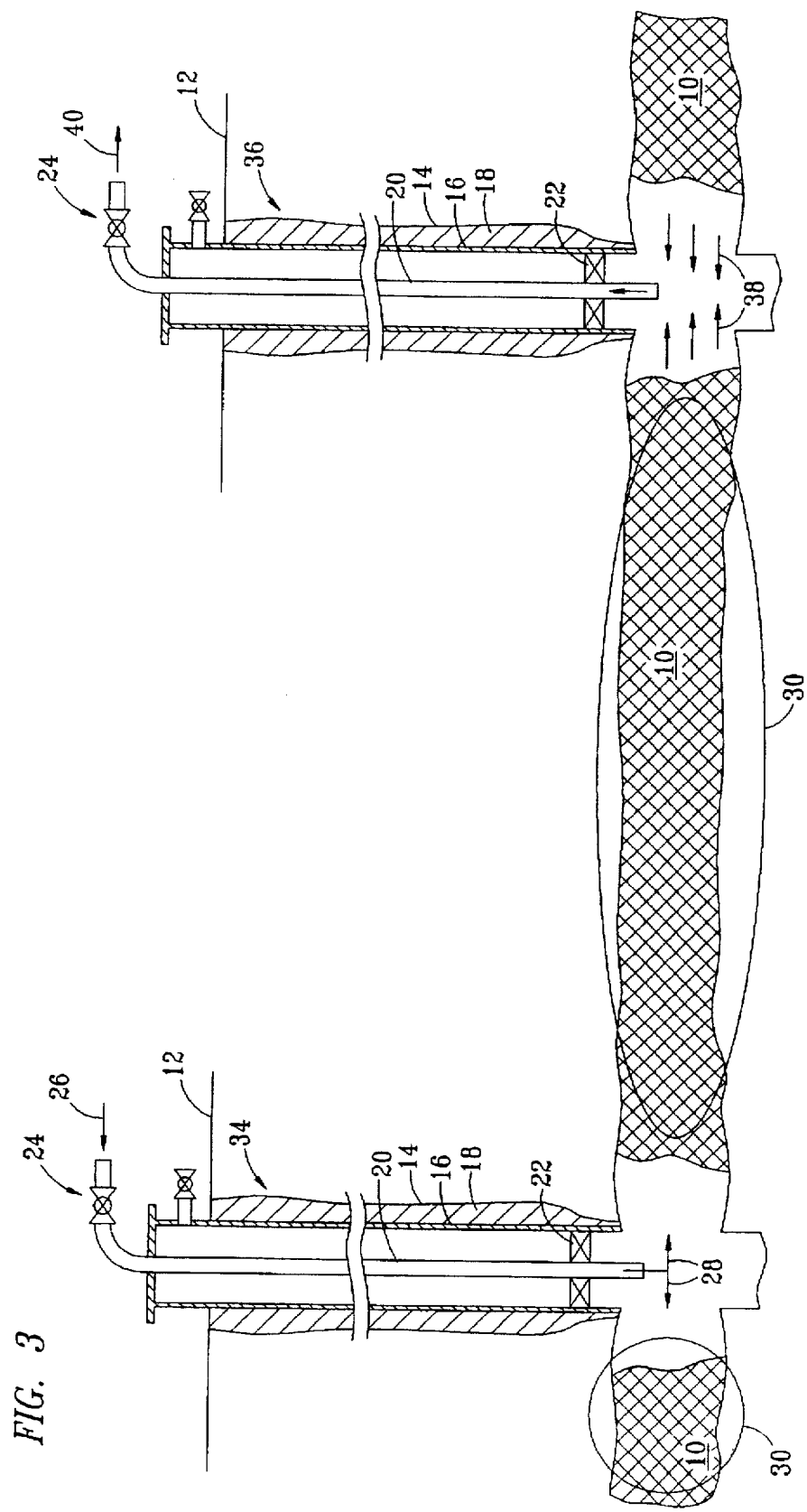
FIG. 3 is a schematic diagram of an injection well and a production well penetrating a subterranean coal formation from the surface.

In the discussion of the Figures, the same numbers will be used throughout to refer to the same or similar components.

In FIG. 1, a coal formation 10 penetrated from a surface 12 by a wellbore 14 is shown. The wellbore 14 includes a casing 16 positioned in the wellbore 14 by cement 18. Alternatively, the casing 16 could extend into or through the coal formation 10 with perforations through the casing in the coal seam providing fluid communication with the coal formation from the casing 16. The wellbore 14 extends into the coal formation 10 and includes a tubing 20 and a packer 22. The packer 22 is positioned to prevent flow between the outer diameter of the tubing 20 and the inner diameter of the casing 16. The wellbore 14 also includes equipment 24 adapted to inject a gaseous or liquid stream into the coal formation 10 or to recover a gaseous or liquid stream from the coal formation 10.

In the practice of the present invention, an aqueous oxidant solution is injected as shown by an arrow 26 through the tubing 20 into the coal formation 10 as shown by arrows 28. The zones treated are shown by circles 30. The aqueous oxidant solution is injected into the coal formation 10 for a selected time to enhance or stimulate the formation of a cleat system in the coal formation 10. The aqueous oxidant solution is injected for a period of time and in a quantity considered sufficient to increase the permeability of the coal formation 10 in the zones 30. After a selected period or after a selected amount of the aqueous oxidant solution has been injected, the well is shut in for a period of time which may be greater than 24 hours. Typically, the well is shut-in until the pressure in the wellbore returns to the formation pressure and thereafter for at least 12 additional hours. The shut-in period allows for migration of the oxidant-containing solution into the coal formation 10 to oxidize components of the coal formation 10 to enhance the cleat system in the coal formation 10. Subsequent to the shut-in period, water is recovered from the coal formation 10 with methane to de-water the coal formation in the zones 30. The term "de-water" as used herein does not refer to the complete removal of water from the coal formation 10, but rather to the removal of sufficient water from the coal formation 10 to open passage ways in the cleat system in coal formation 10 so that methane can be produced through the passage ways from the coal formation 10.

The aqueous oxidant solution contains an oxidant selected from the group consisting of hypochlorite, metallic salts of hypochlorous acid, hydrogen peroxide, ozone, oxygen and combinations thereof. Typically, the oxidant is used in concentrations equal to less than 10 volume percent of the aqueous oxidant solution. When hydrogen peroxide is used, the concentrations are desirably up to about 10 volume percent of the solution with concentrations from 5 to 10 percent being preferred. When hypochlorite is used, concentrations up to 5.0 volume percent are used.

In the embodiment shown in FIG. 1, a single well is used for injection of the aqueous oxidant solution to chemically enhance or stimulate the formation of a cleat system in the zones 30 to result in the release of formation water and an increase in the methane production rate from the coal formation 10.

In FIG. 2, a similar embodiment is shown except that the coal formation 10 has been fractured by fractures 32. The operation of the well is basically the same as that shown in FIG. 1 except that the coal formation 10 has previously been fractured or is fractured by a fluid which may comprise the aqueous oxidant solution during at least part of the fracturing operation. For instance, it may be desirable to use a conventional fracturing application, if the coal formation 10 is sufficiently impermeable, as an initial stimulation method followed by the aqueous oxidant solution as a post-fracturing flush. The post-fracturing flush enhances cleat permeability throughout the areas contacting the fracture. In such instances, the well is desirably shut-in as discussed previously and the oxidants are selected from the same oxidant materials group discussed previously. The fractures are formed in the coal formation 10 prior to injection of the oxidant solution. The oxidant solution could comprise the fracturing fluid if desired.

In FIG. 3, an injection well 34 and a production well 36 penetrate the coal formation 10 from the surface 12. The injection well 34 is spaced apart from the production well 36 at a spacing based upon the characteristics of the particular coal formation and the like. According to the present invention, the aqueous oxidant solution described above is injected into the coal formation 10 through the injection well 34 as shown by the arrow 26 and the arrows 28 to treat the zones 30 which may extend from the injection well 34 in a generally circumferential direction, but generally extend preferentially toward a nearby production well or production wells. The production well 36 is positioned to withdraw water and methane from the coal formation 10. The production of water and methane through the production well 36 causes the aqueous oxidant solution to migrate toward the production well 36. Desirably, injection of the aqueous oxidant solution is continued until an increased water volume is detected in the production well 36 or until detection of an injection "tag" substance indicating the presence of a quantity of the aqueous oxidant solution is detected in the production well 36. The increase in the quantity of water produced from the production well 36 is indicative of the formation or enhancement of cleats in the coal formation 10 with a resulting increase in permeability so that additional quantities of water are released from the coal formation 10 for production as shown by arrows 38 through the production well 36 and a line 40. The arrows 38 are shown directed toward the production well 36 from both directions in contemplation that water will continue to be recovered at a lower rate from untreated portions of the coal formation 10.

The embodiment shown in FIG. 4 is similar to that shown in FIG. 3 except that the coal formation 10 has been fractured by fractures 32. Fractures 32 in the embodiment shown in FIG. 2 can be of substantially any extent. By contrast, in the embodiment shown in FIG. 4, the fractures 32 desirably extend no more than half way to the production well 36. Clearly, if the fractures 32 extend completely into the production well 36, it will be difficult to use any kind of fluid or gas drive between the injection well 34 and the production well 36. Desirably, the fractures extend no more than half the distance between the injection well 34 and the production well 36. The use of the aqueous oxidant solution with the fractures 32 is as discussed previously.

The aqueous oxidant solution comprises a solution of hypochlorite (HOCl), metallic salts of hypochlorous acid (such as NaOCl, and the like), hydrogen peroxide ($H_2O_2$), ozone ($O_3$) solutions, or oxygen ($O_2$) saturated water. Of these materials, solutions of hypochlorite, peroxide and ozone are preferred because they are more readily generated in the relatively high volumes required in the field. Of these, hydrogen peroxide and ozone are preferred because they introduce only hydrogen and oxygen components into the coal formation 10. While hypochlorite, which is household bleach, is available commercially in large quantities at concentrations up to about 5.0 volume percent, the presence of the chlorine may be of concern in some coal formations. Concentrations of hydrogen peroxide and ozone up to about 10 volume percent are suitable, although solutions containing less than about 5.0 volume percent are preferred.

In FIG. 5, a 5-spot well arrangement is shown. Such well arrangements are useful in the practice of the present invention and may be used in a recurring pattern over a wide area. Such arrangements are well known to those skilled in the art and will be discussed only briefly. In the arrangement shown in FIG. 5, the aqueous oxidant solution is injected through the injection well 34 to treat the zones 30 to enhance the recovery of water and methane from the production wells 36. When break-through of the aqueous oxidant solution occurs, as evidenced by the production of water and methane at an increased rate from the production wells 36, the injection of the aqueous oxidant solution is stopped and the injection well 34 can be converted to a production well. The area would then be de-watered through the original production wells and the converted injection well. The areas of enhanced cleat formation will accelerate the de-watering process and increase the methane production rates and the ultimate methane recovery.

The method of the present invention is also useful as a pre-treatment for gas injection treatments to enhance the recovery of methane from the coal formation 10. The use of carbon dioxide, either alone or with other gases, to increase the production of methane from coal formations is well known. Similarly, the use of inert gases, such as nitrogen, argon and the like, to remove additional quantities of methane from coal formations by increasing the pressure in the formation and thereby removing additional methane as the methane partial pressure in the atmosphere in the coal seam is decreased are well known to those skilled in the art. The use of such processes requires that the formation be permeable to gas flow into or through the formation so that the methane can be recovered. The method of the present invention enhances the permeability of coal formations and may be used prior to the use of gas sweep or gas desorption treatments to enhance the recovery of methane.

Having thus described the present invention by reference to certain of its preferred embodiments, it is noted that the embodiments discussed are illustrative rather than limiting in nature and that many variations and modifications are possible within the scope of the present invention. Many such variations and modifications may be considered obvious and desirable by those skilled in the art based upon a review of the foregoing description of preferred embodiments.

Having thus described the invention, we claim:

1. A method of enhancing the permeability to methane of a water-containing subterranean coal formation having a low permeability to methane penetrated by at least one well, the method consisting essentially of:
   a) injecting an aqueous oxidant solution into the coal formation;
   b) maintaining the aqueous oxidant solution in the coal formation for a selected time to stimulate the formation of cleats in the coal formation;
   c) producing methane from the coal formation at an increased rate.

2. The method of claim 1 wherein the aqueous oxidant solution comprises an aqueous solution of an oxidant selected from the group consisting of hydrogen peroxide, ozone, oxygen and combinations thereof.

3. The method of claim 2 wherein sufficient water is removed from the coal formation to open passageways in the cleats in the coal formation.

4. The method of claim 2 wherein the aqueous oxidant solution is an aqueous solution of hydrogen peroxide.

5. The method of claim 2 wherein the aqueous oxidant solution is an aqueous solution of ozone.

6. The method of claim 2 wherein the aqueous oxidant solution is oxygen saturated water.

7. The method of claim 2 wherein the aqueous oxidant solution contains up to about 10 volume percent of the oxidant.

8. The method of claim 2 wherein the aqueous oxidant solution contains up to about 5 volume percent of the oxidant.

9. The method of claim 1 wherein the aqueous oxidant solution is injected into the coal formation through a first well; the first well is shut-in for a selected time; and thereafter, methane is produced from the first well at an increased rate.

10. The method of claim 1 wherein the coal formation has been fractured with fractures extending from the well prior to injection of the aqueous oxidant solution.

11. The method of claim 1 wherein the aqueous oxidant solution comprises a fracturing fluid injected at fracturing conditions to fracture the coal formation.

12. The method of claim 1 wherein said aqueous oxidant solution is maintained in the coal formation for at least 24 hours.

13. A method for increasing the permeability to methane of a water-containing subterranean coal formation having a low permeability to methane penetrated by at least one injection well and at least one production well, the method consisting essentially of:
   a) injecting an aqueous oxidant solution into the coal formation through the injection well;
   b) maintaining the aqueous oxidant solution in the coal formation for a selected time to stimulate the formation of cleats in the coal formation; and
   c) producing methane from the coal formation through the production well at an increased rate.

14. The method of claim 13 wherein the aqueous oxidant solution comprises an oxidant selected from the group consisting of hypochlorite, metallic salts of hypochlorous acid, hydrogen peroxide, ozone, oxygen and combinations thereof.

15. The method of claim 14 wherein the aqueous oxidant solution contains up to about 10 volume percent of the oxidant.

16. The method of claim 14 wherein the aqueous oxidant solution contains up to about 5 volume percent of the oxidant.

17. The method of claim 14 wherein the oxidant is selected from the group consisting of hydrogen peroxide and ozone.

18. The method of claim 13 wherein sufficient water is recovered through the production well to open passageways in the cleats in the coal formation.

19. A method for increasing the production of methane from a water-containing subterranean coal formation penetrated by at least one injection well and at least one production well, the method comprising:
   a) injecting an aqueous oxidant solution into the coal formation through the injection well until water is recovered from the production well at an increased rate; and,
   b) producing methane from the coal formation through the production well at an increased rate.

* * * * *